US012649011B2

(12) United States Patent
Musa et al.

(10) Patent No.: US 12,649,011 B2
(45) Date of Patent: Jun. 9, 2026

(54) RELEASE DEVICE

(71) Applicant: Delox—Investigação, Processos e Equipamentos Científicos, LDA, Cascais (PT)

(72) Inventors: Fadhil Yussof Musa, Cascais (PT); Fernando José Nunes Antunes, Cascais (PT); João Manuel Pires da Silva, Cascais (PT)

(73) Assignee: Delox—Investigação, Processos e Equipamentos LDA, Cascais (PT)

( * ) Notice: Subject to any disclaimer, the term of this patent is extended or adjusted under 35 U.S.C. 154(b) by 950 days.

(21) Appl. No.: 17/786,642

(22) PCT Filed: Dec. 18, 2020

(86) PCT No.: PCT/IB2020/062223
§ 371 (c)(1),
(2) Date: Dec. 7, 2022

(87) PCT Pub. No.: WO2021/124276
PCT Pub. Date: Jun. 24, 2021

(65) Prior Publication Data
US 2023/0130091 A1 Apr. 27, 2023

Related U.S. Application Data

(60) Provisional application No. 62/949,612, filed on Dec. 18, 2019.

(51) Int. Cl.
*A61L 9/03* (2006.01)

(52) U.S. Cl.
CPC ......... *A61L 9/032* (2013.01); *A61L 2209/133* (2013.01); *A61L 2209/135* (2013.01); *A61L 2209/14* (2013.01)

(58) Field of Classification Search
CPC ...................................................... A61L 9/032
See application file for complete search history.

(56) References Cited

U.S. PATENT DOCUMENTS 2,986,448 A 5/1961 Gates et al.
3,480,557 A 11/1969 Shiraeff et al.
(Continued)

FOREIGN PATENT DOCUMENTS

EP 1121980 A1 8/2001
EP 1557181 A1 7/2005
(Continued)

OTHER PUBLICATIONS

Dabrowski et al., "Comparison of energy-distribution functions calculated for gas-solid and liquid-solid adsorption data", Colloids and Surfaces A: Physicochem. Eng. Aspects 212, 2003, pp. 109-114.
(Continued)

*Primary Examiner* — Kevin Joyner
(74) *Attorney, Agent, or Firm* — The Webb Law Firm

(57) ABSTRACT

Provided is a release device including a housing having an inlet and an outlet, a heating element arranged in the housing, a first fan arranged to move air into the inlet and around the heating element, and a second fan arranged to move vapor out of the outlet. Other embodiments and arrangements are disclosed.

7 Claims, 13 Drawing Sheets

FAN FOR OUTWORD FLOW 112

MIXTURE OF AIR AND GASEOUS HYDROGEN PEROXIDE

AIR AT AMBIENT TEMPERATURE

EXIT FILTER 116

ENTRANCE FILTER 118

FAN FOR INWARD FLOW 114

AIR AT AMBIENT TEMPERATURE

RESISTANCE

110

100

(56) References Cited

U.S. PATENT DOCUMENTS

| | | | |
|---|---|---|---|
| 3,870,783 A | | 3/1975 | Hall et al. |
| 4,839,157 A | | 6/1989 | Ng et al. |
| 4,891,211 A | | 1/1990 | Winston |
| 5,077,047 A | | 12/1991 | Biss et al. |
| 5,667,753 A | | 9/1997 | Jacobs et al. |
| 5,674,450 A | | 10/1997 | Lin et al. |
| 5,770,739 A | | 6/1998 | Lin et al. |
| 5,820,841 A | | 10/1998 | Chen et al. |
| 5,876,666 A | | 3/1999 | Lin et al. |
| 5,904,897 A | * | 5/1999 | Kendall .................... A61L 2/26 |
| | | | 428/35.8 |
| 5,993,748 A | * | 11/1999 | Wheeler .............. A61M 11/042 |
| | | | 392/390 |
| 6,371,451 B1 | * | 4/2002 | Choi ................... B01F 23/2132 |
| | | | 261/DIG. 89 |
| 8,889,044 B2 | | 11/2014 | Yano et al. |
| 2013/0343951 A1 | | 12/2013 | Wuest et al. |
| 2016/0051928 A1 | | 2/2016 | Spiegelman et al. |

FOREIGN PATENT DOCUMENTS

| | | |
|---|---|---|
| EP | 1646708 A2 | 4/2006 |
| EP | 1701746 A1 | 9/2006 |
| JP | 4921649 B2 | 4/2012 |
| WO | 2004104154 A3 | 1/2005 |

OTHER PUBLICATIONS

Giaya et al., "Liquid and vapor phase adsorption of chlorinated volatile organic compounds on hydrophobic molecular sieves", Microporous and Mesoporous Materials 40, 2000, pp. 205-218.

Goncalves et al., "Adsorption of hidrogen peroxide on the surface of silica—titania mixed oxide obtained by the sol-gel processing method", Ecletica Quimico, 2007, pp. 41-45, vol. 32, No. 2.

Kwon et al., "Silica-based mesoporous nanoparticles for controlled drug delivery", Journal of Tissue Engineering, Feb. 2013, pp. 1-18.

Lewandowski et al., "Adsorption of hydrogen peroxide on functionalized mesoporous silica surfaces", Structural Chemistry, 2014, pp. 1505-1512.

Li et al., "Magnetic microsphere to remove tetracycline from water: adsorption, H2O2 oxidation and regeneration", Chemical Engineering Journal, 2017, 37 pages.

Lv et al., "Adsorption behaviors and vibrational spectra of hydrogen peroxide molecules at quartz/water interfaces", Phys. Chem. Chem. Phys., 2017, pp. 7054-7061.

McDonnell, "The use of hydrogen peroxide for disinfection and sterilization applications", PATAI's Chemistry of Functional Groups, 2014, John Wiley & Sons, Ltd., 34 pages.

Pham, "Activation of Hydrogen Peroxide by Iron-Containing Minerals and Catalysts in Circumneutral pH Solutions: Implications for ex situ and in situ Treatment of Contaminated Water and Soil", 2012 UC Berkeley Thesis, 135 pages.

Pradhan et al., "Heterogeneous uptake of gaseous hydrogen peroxide by Gobi and Saharan dust aerosols: a potential missing sink for H2O2 in the troposphere", Atmospheric Chemistry and Physics, 2010, pp. 11081-11107.

Sripathi et al., "Vapor phase versus liquid phase grafting of mesoporous alumina", Microporous and Mosoporous Materials 172, 2013, pp. 1-6.

Wolanov et al., "Aqueous stability of alumina and silica perhydrate hydrogels: experiments and computations", Dalton Transactions, 2014, 12 pages.

Zeglinski et al., "Silica xerogel-hydrogen peroxide composites: Their morphology, stablity, and antimicrobial activity", Colloids and Surfaces B: Biointerfaces, 2007, pp. 165-172.

Zhao et al., "Kinetics and Mechanisms of Heterogeneous Reaction of Gaseous Hydrogen Peroxide on Mineral Oxide Particles," Environmental Science & Technology, 2011, pp. 3317-3324.

* cited by examiner

AIR AT AMBIENT TEMPERATURE

MIXTURE OF AIR AND GASEOUS HYDROGEN PEROXIDE

ENTRANCE FILTER 118

FAN FOR INWARD FLOW 114

EXIT FILTER 116

FAN FOR OUTWORD FLOW 112

RESISTANCE

AIR AT AMBIENT TEMPERATURE

100

110

210

200

410

412

414

416

418

420

422

410

412

413

414

416

418

420

422 electronics area intake fan display / touchscreen air intake and heating

1 - Axial Fan
2 - Exit Filter
3 - Glass Vial
4 - Entry Filter
5 - High Pressure Fan
6 - Electric Heater
7 - Electronics/Control
8 - Air Outlet
9 - Air Inlet

8

SECTION A-A

HEATING MODULE FOR THE TOP
OF THE CONSUMABLE
CONTAINING DRY VAPORIZABLE
HYRDROGEN PEROXIDE (VHP)
FORMULATION (174)

DEVICE SCREEN

DEPOSIT FOR AERATION
FORMULATION (172)

DEPOSIT FOR THE
CONSUMABLE CONTAINING
DRY VAPORIZABLE
HYDROGEN PEROXIDE (VHP)
FORMULATION (171)

RELEASE DEVICE

CROSS-REFERENCE TO RELATED APPLICATIONS

This application is the United States national phase of International Application No. PCT/IB2020/062223 filed Dec. 18, 2020, and claims priority to U.S. Provisional Application No. 62/949,612 filed Dec. 18, 2019, the disclosures of which are hereby incorporated in their entirety by reference.

BACKGROUND

1. Field

This disclosure relates generally to a vapor release device.

BRIEF DESCRIPTION OF THE DRAWINGS

Additional advantages and details are explained in greater detail below with reference to the exemplary embodiments that are illustrated in the accompanying schematic figures, in which.

SUMMARY

Figure 1:
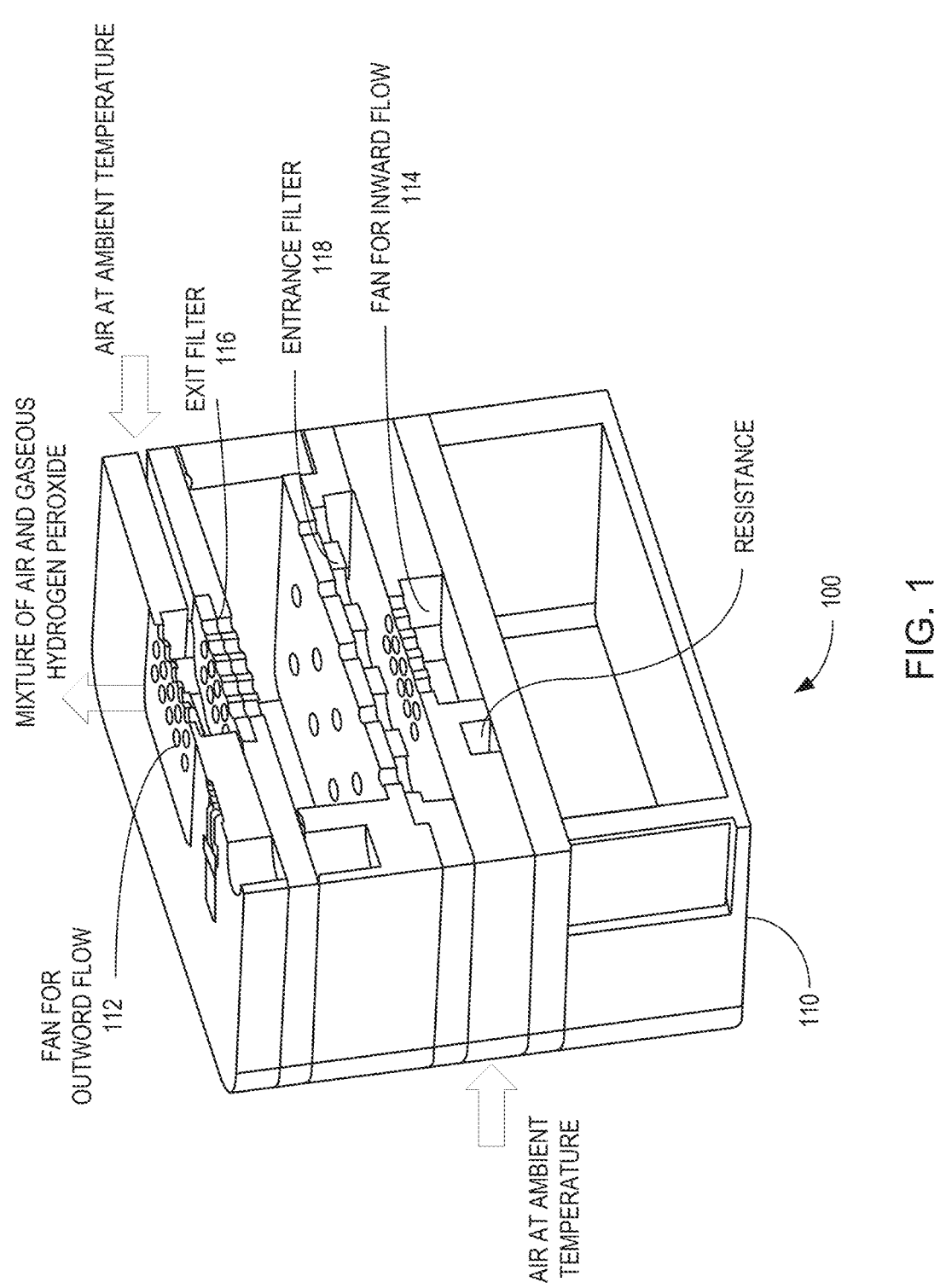
FIG. 1 illustrates a cross-sectional view of a release device according to a non-limiting embodiment.

According to non-limiting embodiments or aspects, provided is a release device, comprising a housing including an inlet and an outlet; a heating element arranged in the housing; a first fan arranged to move air into the inlet and around the heating element; and a second fan arranged to move vapor out of the outlet.

In non-limiting embodiments or aspects, the heating element comprises a metallic plate. In non-limiting embodiments or aspects, the first fan is arranged below the heating element. In non-limiting embodiments or aspects, the housing comprises a lid, and the second fan is arranged in the lid. In non-limiting embodiments or aspects, the release device further comprises a cavity positioned above the heating element and configured to receive a cartridge containing a solid compound.

According to non-limiting embodiments or aspects, provided is a release device, comprising: a funnel-shaped container including an inlet and an outlet; a first filter covering the inlet; a second filter covering the outlet; and a heating element configured to input heated air into the inlet of the funnel-shaped container.

In non-limiting embodiments or aspects, the release device further comprises at least one input device configured to adjust at least one of a temperature and velocity of the heated air. In non-limiting embodiments or aspects, the heated air has a temperature of 60° C. to 90° C.

According to non-limiting embodiments or aspects, provided is a release device, comprising: a funnel-shaped container including an inlet and an outlet; a first filter covering the inlet; a second filter covering the outlet; a fan with a heating element; and an aeration module.

In non-limiting embodiments or aspects, the release device further comprises at least one input device configured to adjust at least one of a temperature and velocity of the heated air. In non-limiting embodiments or aspects, the heated air has a temperature of 60° C. to 90° C. In non-limiting embodiments or aspects, the heated air is heated by at least one fan with at least one heating element. In non-limiting embodiments or aspects, the heated air is circulated by at least one fan. In non-limiting embodiments or aspects, the heated air is circulated by the fan with a heating element. In non-limiting embodiments or aspects, the fan with a heating element controls the exit air temperature. In non-limiting embodiments or aspects, the aeration module intakes air from the release device's surroundings. In non-limiting embodiments or aspects, the first filter covering the inlet filters in heated air. In non-limiting embodiments or aspects, the second filter covering the outlet filters out vaporized hydrogen peroxide.

According to non-limiting embodiments or aspects, provided is a release device comprising: a cavity adapted to receive a cassette comprising a powdered hydrogen peroxide formulation; an air intake; a heating element configured to heat air received through the air intake and to pass the heated air through the cassette placed in the cavity to release hydrogen peroxide-enriched air; and a fan to release the hydrogen peroxide-enriched air into a surrounding environment. In non-limiting embodiments or aspects, the release device further comprises: a second cavity adapted to receive a second cassette comprising a catalyzer material; and a controller configured to alter an airflow from the air intake to the second cavity to bypass the first cavity. In non-limiting embodiments or aspects, the controller is in communication with and controls operation of the heating element, the fan, and a second fan.

DETAILED DESCRIPTION

For purposes of the description hereinafter, the terms "end," "upper," "lower," "right," "left," "vertical," "horizontal," "top," "bottom," "lateral," "longitudinal," and derivatives thereof shall relate to the embodiments as they are oriented in the drawing figures. However, it is to be understood that the embodiments may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

A release device is provided to disperse a vapor from a compound that is absorbed/adsorbed into solid particles.

According to a first non-limiting embodiment, a cross-sectional view of which is shown in FIG. 1, a release device 100 includes a housing 110, a metallic plate, and two fans 112, 114 (a fan underneath the metallic plate 114 and a second fan 112 on top of the lid). It will be appreciated that other heating elements may be used, such as a ceramic plate, a ceramic or metallic coil, and/or the like. A power source is used to heat the metallic plate with resistive heating. In some non-limiting embodiments, the metallic plate may be heated up to 90° C. However, it will be appreciated that various temperatures may be used depending on the particle being released. The fan underneath the metallic plate facilitates the release of the vapor from the particles and movement of the vapor upwards. The fan on top of the lid of the housing disperses the vapor into the surrounding atmosphere or space. The release device includes an entrance filter 118 and an exit filter 116.

Figure 2:
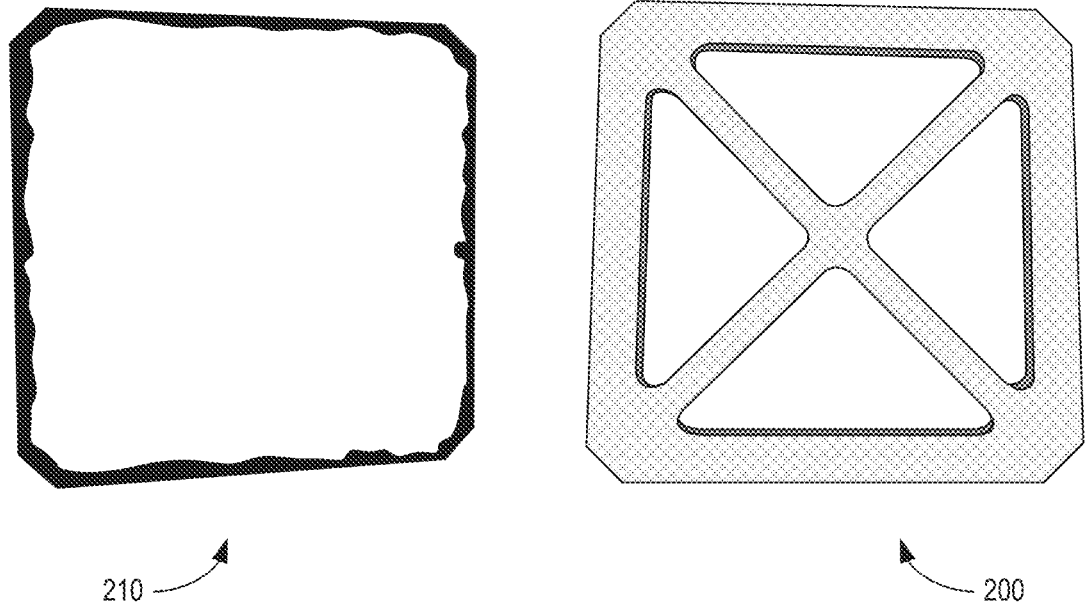
FIG. 2 illustrates a cartridge for use in a release device according to a non-limiting embodiment.

In operation, a cartridge (e.g., a cassette or other device) including a compound is placed on the metallic plate. A cartridge 200 is shown in FIG. 2 according to a non-limiting embodiment. A cartridge 200 may include a permeable fabric 210 on a bottom side and a filter on a top side such that a compound is held between the bottom side and the top side. The cartridge may be sized and shaped so as to be inserted into the housing of the release device and to be arranged on or near the metallic plate or other heating element.

Once the cartridge is inserted or placed in the release device, air at an ambient temperature may enter one or more openings in the housing. The heated plate, in turn, heats the air and/or the cartridge (and the compound contained therein). The heated air passes through the solid particles which releases vapor.

Figure 3:
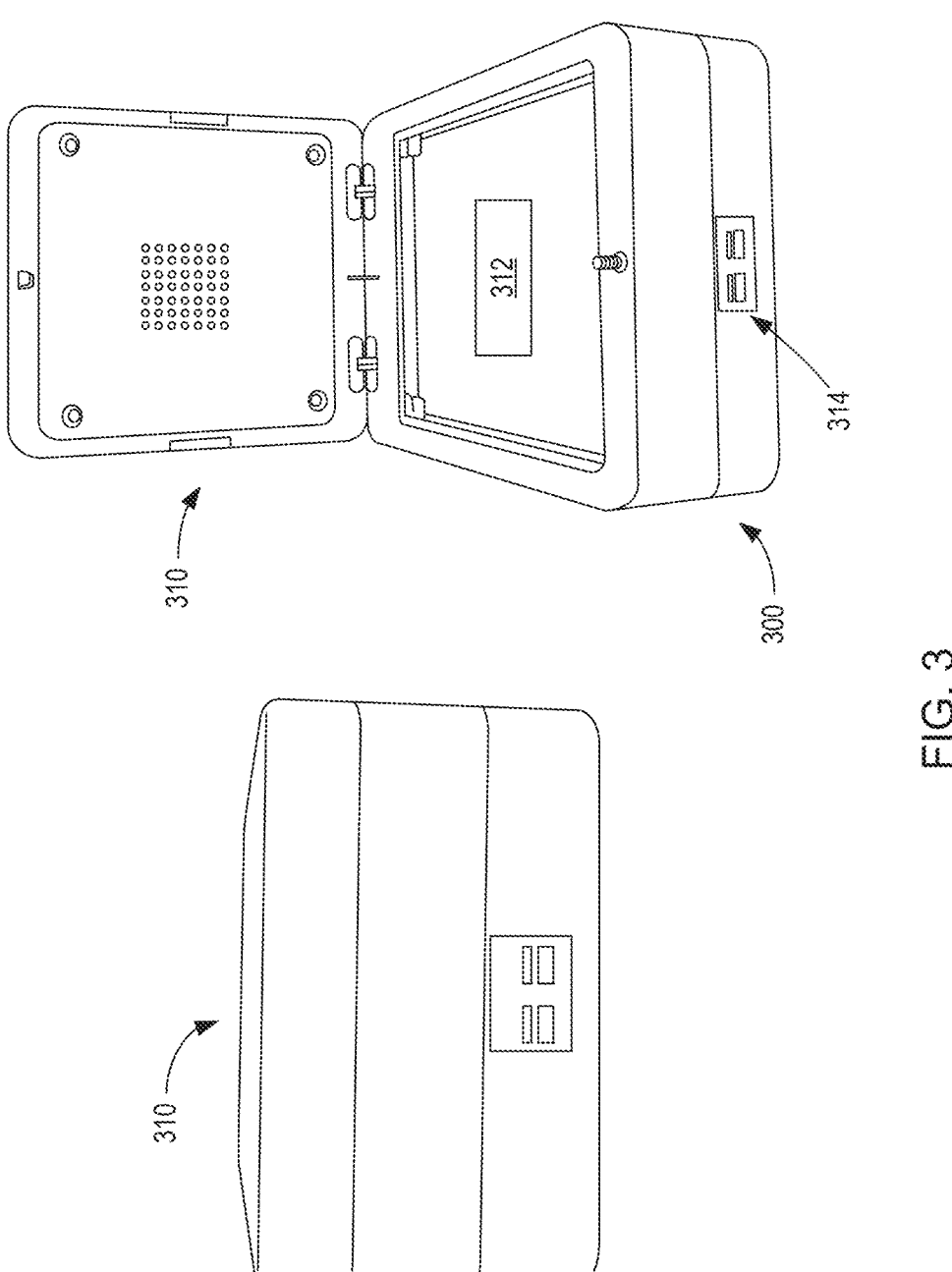
FIG. 3 illustrates a release device according to a non-limiting embodiment.

Referring now to FIG. 3, a release device 300 is shown according to a non-limiting embodiment. As shown, the release device 300 has a lid 310 that opens with hinges, apertures in the underside of the lid, a metallic plate 312 in a cavity of the bottom portion of the housing, a control panel 314, and a switch. It will be appreciated that various arrangements and implementations may be used.

Figure 4:
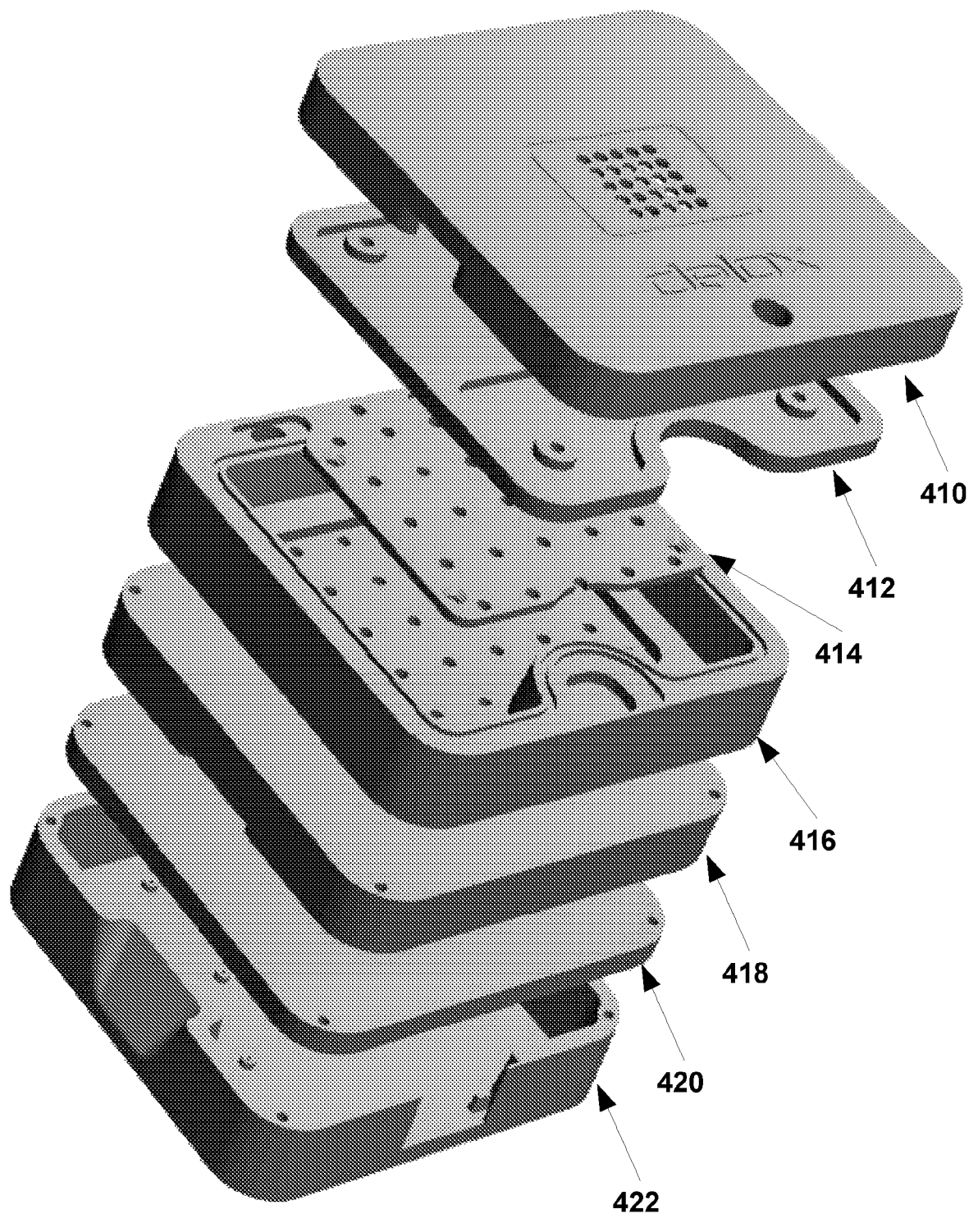
FIGS. 4-5 illustrate exploded views of the release device of FIG. 1 according to a non-limiting embodiment.
Figure 5:
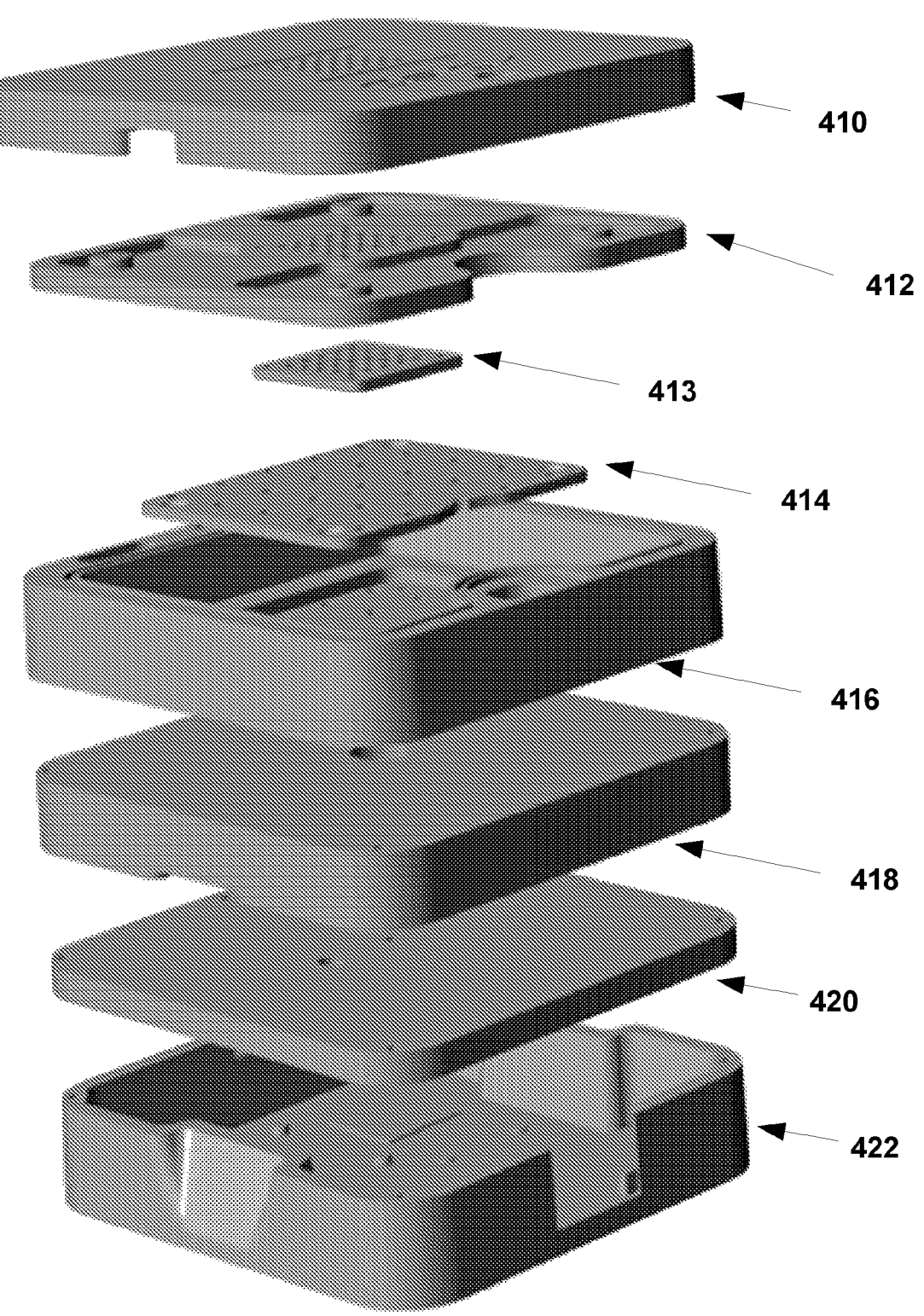

FIGS. 4 and 5 show exploded views of the non-limiting embodiment of the release device shown in FIG. 1. From top to bottom, the components are as follows: lid with outlet 410; housing 412 for exit fan; exit filter 413 (attached to bottom of housing for exit fan); entrance filter 414 (attached to top of housing 416 for cassette); housing 416 for cassette or compound and entrance filter; housing 418 for heating element and entrance fan; and base 422 and housing 420 for electronic components.

Figure 6:
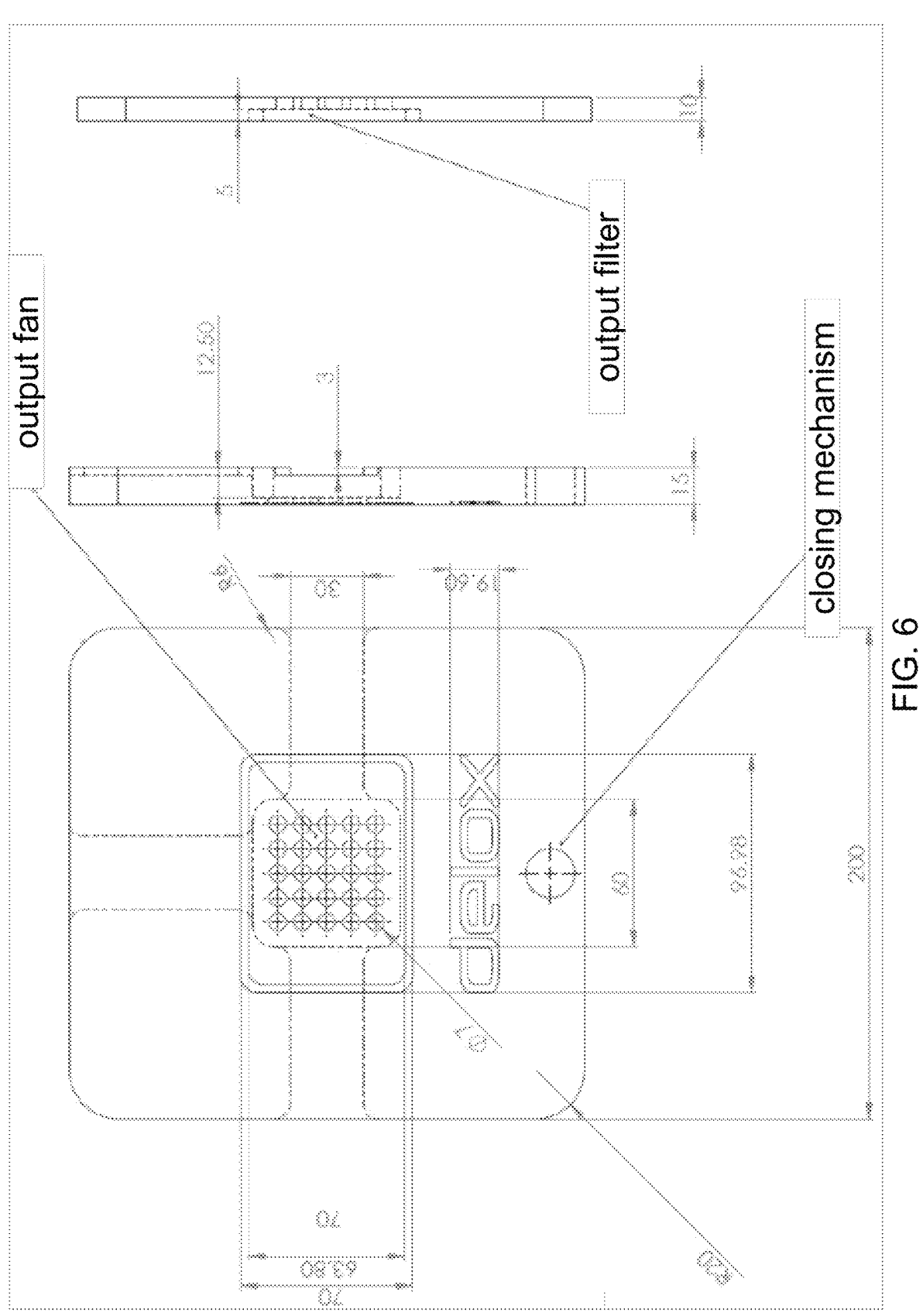
FIGS. 6-11 illustrate components of the non-limiting embodiment of the release device shown in FIG. 1.
Figure 7:
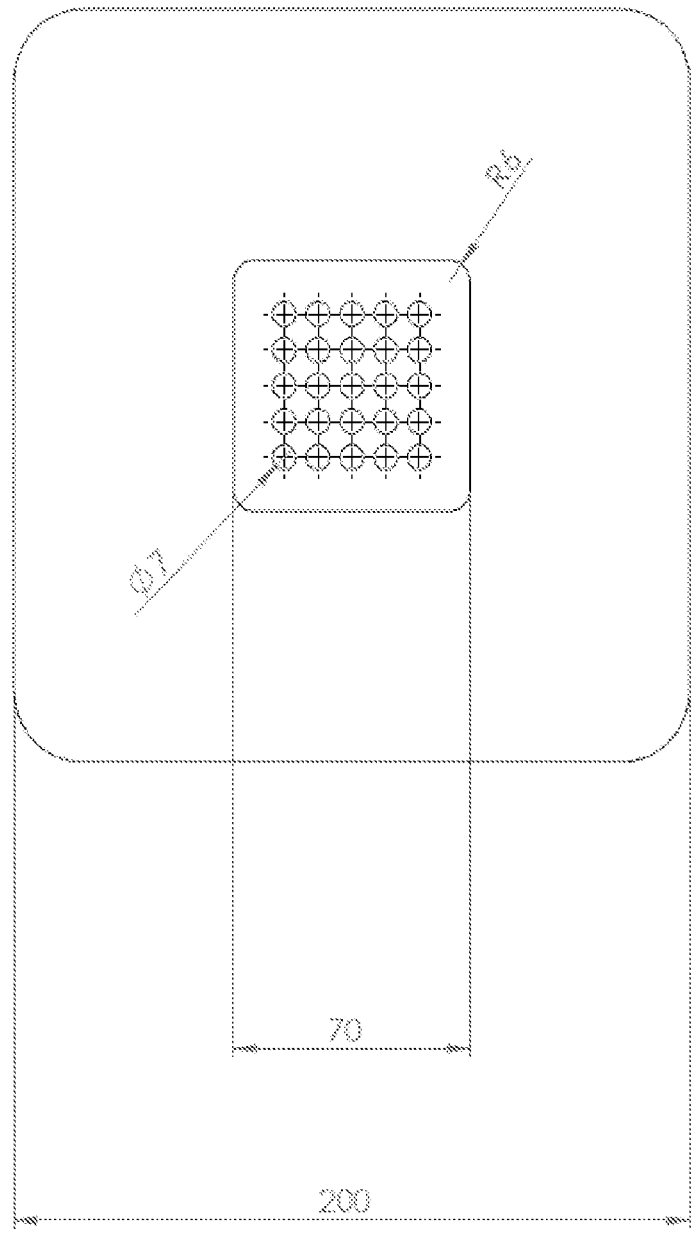
Figures 8, 9:
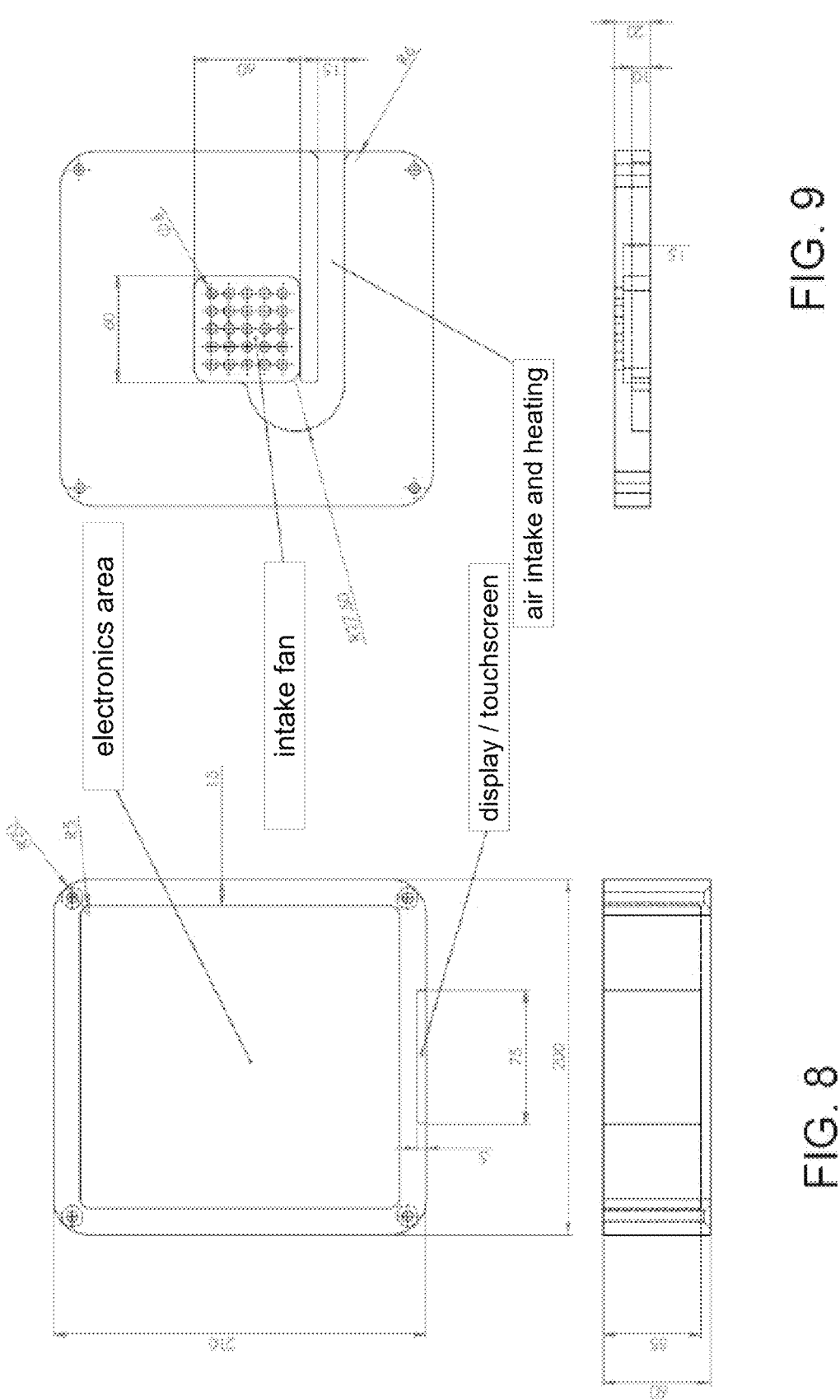

FIGS. 6-8 show components of the non-limiting embodiment of the release device shown in FIG. 1. The dimensions and arrangements shown in FIGS. 6-8 are for illustrative purposes only.

FIG. 6 is a top view and a side view of a lid of a release device according to a non-limiting embodiment. As shown, the lid includes a filter arranged over an outlet such that vapor produced in the release device is outputted through the filter. FIG. 7 is a bottom view of the lid.

FIG. 8 shows a top view and a side view of a section of the release device containing the electronic controlling elements according to a non-limiting embodiment. A control panel (e.g., an input device) is arranged on an exterior housing of the release device for receiving user input.

FIG. 9 shows a top view and a side view of an intake fan of a release device according to a non-limiting embodiment.

Figures 10, 11:
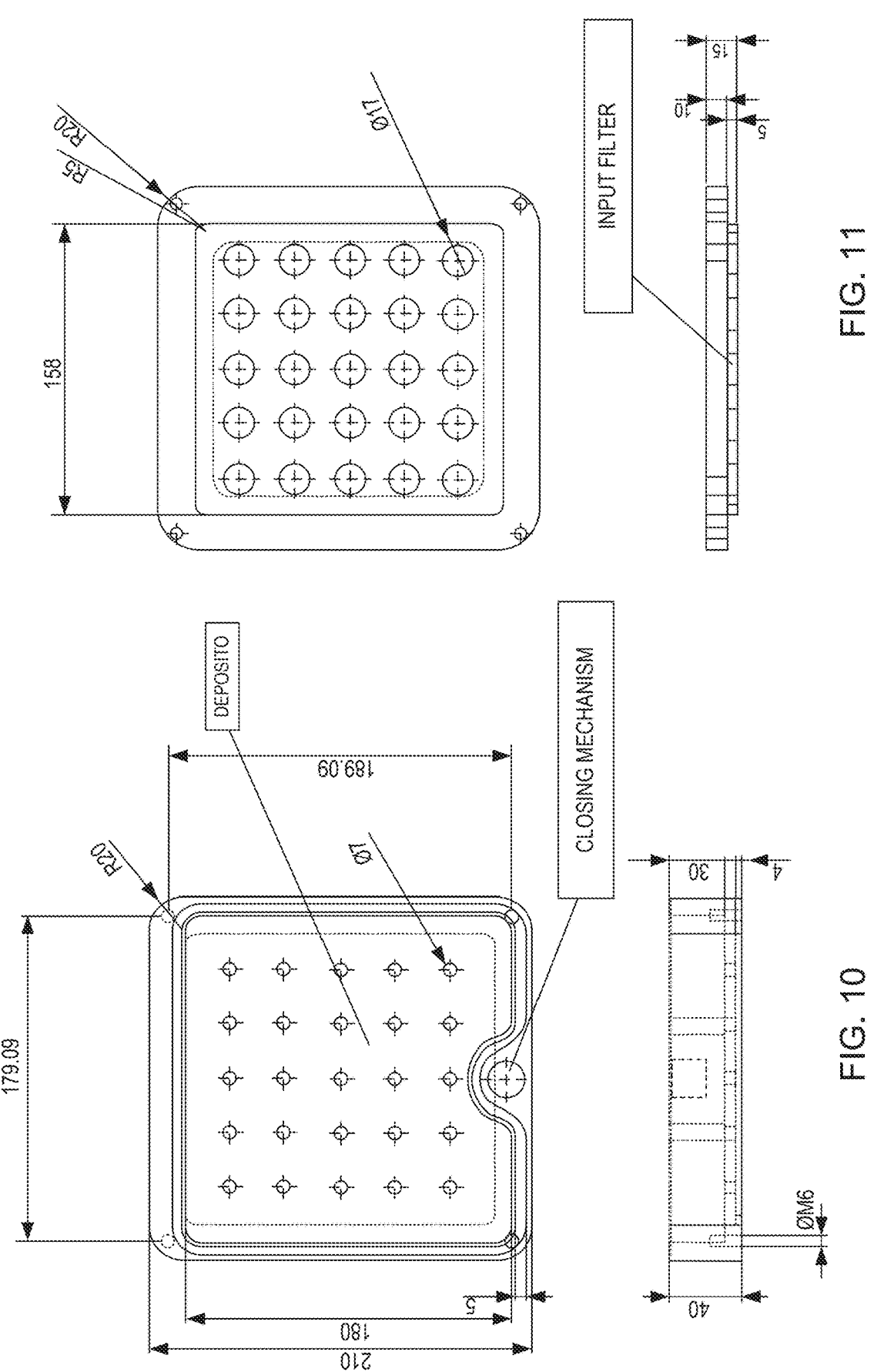

FIG. 10 shows a top view and a side view of a receiving area of a release device according to a non-limiting embodiment. The receiving area receives a compound, such as a compound included in a cartridge or otherwise placed in the area. A heating element is arranged in a cavity of the release device. FIG. 11 shows a top view and a side view of an input filter device according to a non-limiting embodiment. The input filter device moves air from outside of the release device to inside the release device through an inlet in a housing of the release device.

Figure 12:
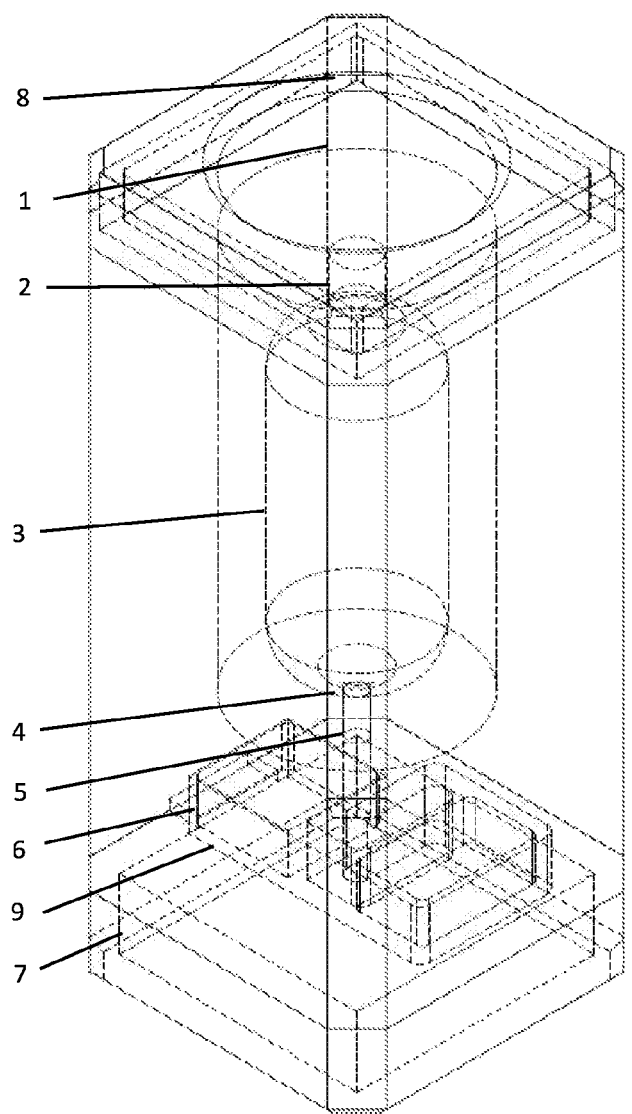
FIGS. 12-14 illustrate a release device according to another non-limiting embodiment.
Figures 13, 14:
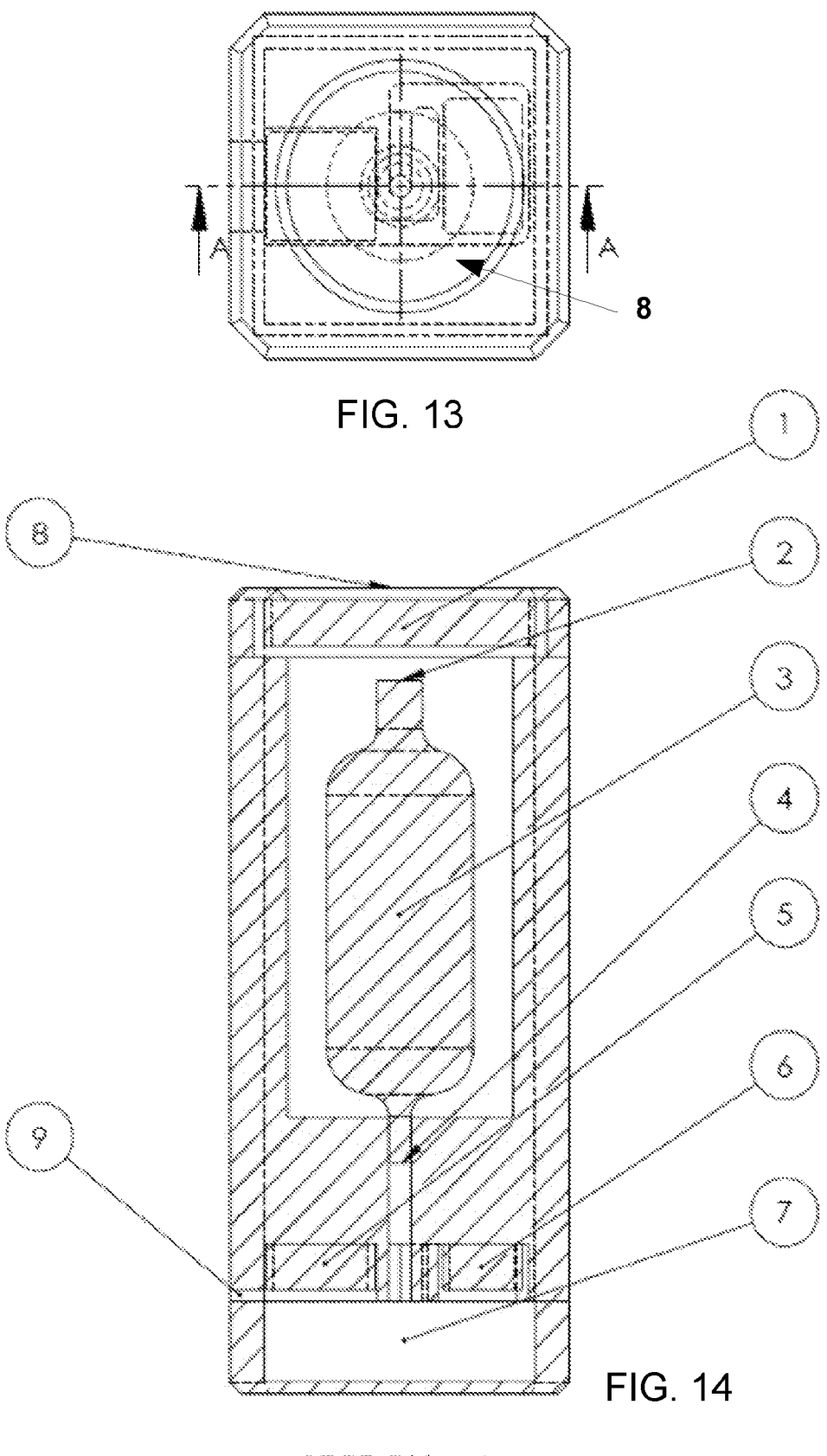

Referring now to FIGS. 12-14, a release device is shown according to a further non-limiting embodiment. FIG. 12 depicts a perspective view of a release device. FIG. 13 depicts a top view of the release device shown in FIG. 12.

FIG. 14 shows a cross-sectional view of the release device shown in FIG. 12 through the line A-A shown in FIG. 13. A top of the release device includes an outlet (8) coupled with a fan (1). An inlet (9) toward a bottom end of the release device provides air into the release device from the surrounding atmosphere. Circuitry, one or more processors, and/or other electronic components (7) may be arranged in a bottom end of the release device or elsewhere. A high pressure fan (5) is coupled to the inlet to pull air into the release device. A heating element (6) is arranged in the release device to heat the air that is received through the inlet (9). The heated air is forced through an entry filter (4) in the release device, although it will be appreciated that the entry filter (4) may also filter the intake air before it is heated. The heated air then moves into a container (3), such as a glass vial, having a bottom opening and a top opening. The container (3) may be of various shapes and, in some non-limiting embodiments, may be funnel-shaped. An exit filter (2) is arranged at the top opening.

With continued reference to FIG. 14, in operation a compound is placed in the container (3) and electricity is supplied to the release device. The heated air that enters the container (3) heats and/or agitates the compound, releasing vapor that passes through the exit filter (2) and the outlet (8), aided by the fan (1) coupled to the outlet (8). It will be appreciated that, in some non-limiting embodiments, a single fan may be used at the inlet or outlet to move air into and/or out of the release device.

With continued reference to FIG. 14, the container (3) may be made from a material such as glass, Teflon®, or polypropylene. A bottom side of the container may include one or more apertures as an air inlet (9). One or more of the filters (2), (4) may include a porous glass or nylon filter, as examples, that block solid particles (e.g., blocking particles having dimensions ranging from 40 to 200 μm, as one possible non-limiting example). Hot air (e.g., between approximately 60° C. to 90° C.) is blown in through the filter (4) to release a vapor from a compound that is absorbed/adsorbed into solid particles. The heated air may be provided by, for example, a heat gun, one or more heating elements (6) and fans (5), and/or the like. The movement of the particles under the action of the air flow will facilitate heat transfer and removal of vapor stored in the solid compound. The vapor is then forced through the outlet and the vapor is dispersed into the surrounding space. The release device may include one or more input devices and/or controls to adjust temperature, air velocity, air pressure, and/or the like to optimize the release of the vapor.

Figure 15:
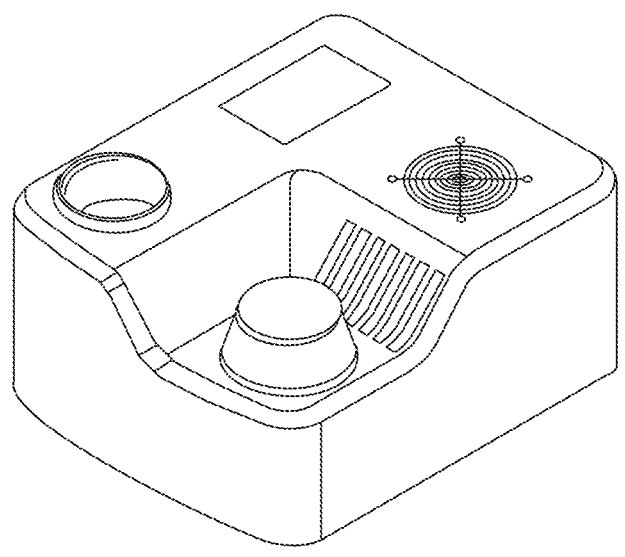
FIGS. 15-17 illustrate a release device according to other non-limiting embodiments.

FIG. 15 shows a non-limiting embodiment of a bio-decontamination device that relies on hot air to fluidize the dry vaporizable hydrogen peroxide (VHP) formulation.

Figure 16:
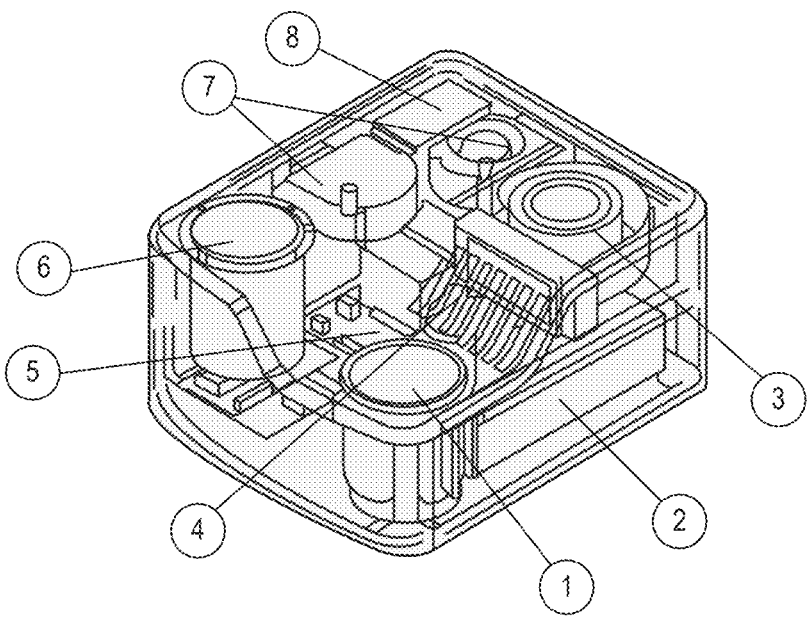

FIG. 16 shows a non-limiting embodiment of the components of the bio-decontamination device shown in FIG. 15. A bio-decontamination device assembly may include: a site (1) adapted to introduce a cassette containing a dry VHP formulation; a pressurization and air heating element (2) arranged to pressurize and/or heat the dry VHP formulation in the cartridge; a fan (3) including a heating element; a fan (4) that delivers air to the cartridge at site (1); an electronic control unit (5); a site (6) to introduce a cassette containing the aeration formulation; fans (7) that diffuse the air around the unit; and a touchscreen (8) or other input device. The electronic control unit (5) may be in electrical communication with the pressurization and air heating element (2) and fans (3) (7) to control these devices.

As shown in FIG. 16, in a non-limiting embodiment ambient air enters through the fan (4) and flows through the pressurization and air heating element (2), where it is rapidly heated before passing through the cylindrical cassette (which may be any shape and/or size in non-limiting embodiments) including the dryVHP formulation with the cassette arranged inside the bio-decontamination site (1). At site (1), the hot air enters the device through a filter that impedes dryVHP powder from being dropped into other components or areas of the device and forces the dryVHP formulation to randomly move (i.e., fluidization). In this process, the hot air removes hydrogen peroxide vapor which exits through a filter (which may be the same type of filter as the entrance filter or a different type of filter) that impedes dryVHP powder from being released while enabling hydrogen peroxide-enriched air to exit. The hydrogen peroxide-enriched air may include vapor and/or a combination of vapor and microdroplets. The filter may be a HEPA filter, for example, that blocks 99.97% of particles that are larger than 0.3 micrometers. The filter may also include a TYVEK filter, in addition to or alternatively to, the HEPA filter. A TYVEK filter may reduce the rate of released hydrogen peroxide-enriched air and/or may block the microdroplets, letting only the vapor escape. It will be appreciated that various filters and combinations of filters may be used to control the nature and amount of the hydrogen peroxide-enriched air that is released. For example, for certain applications with sensitive electronic components, it may be desired to block microdroplets but not vapor because the microdroplets may be more corrosive than the vapor. The fan (3) also releases hot air (e.g., by heating the air that passes through it) to help disperse hydrogen peroxide vapor in the closed environment while also maintaining the desired temperature at the exit filter.

With continued reference to FIG. 16, two outer fans (7) without a heating element also aid the spread of the hydrogen peroxide vapor in the closed environment. In site (6), another cylindrical cassette is placed that includes an aeration formulation including a catalyzer, between a bottom and top filter (which may be the same type of filter as used at site (1)). When the bio-decontamination module is finished, the prototype alters its air flow from site (1) to site (6). As a result, the air enters through site (4) but it is not heated as it flows towards site (6), where the hot air enriched in hydrogen peroxide is mixed with the catalyzer to promote hydrogen peroxide decomposition into water and oxygen and its consequent release. As a result of this process, the closed environment in which the release device is used is bio-decontaminated and no hydrogen peroxide should be present.

In other non-limiting embodiments, the fan (3) with a heating element will help circulate released vaporized hydrogen peroxide in the surroundings by providing air flow into the surroundings and may also control the exit air temperature. In some non-limiting embodiments, the release device may contain additional fans, without heating elements, to further aid circulation of vaporized hydrogen peroxide in the surrounding area.

In another non-limiting embodiment, an aeration module may be configured to stop the bio-decontamination process. For example, after the bio-decontamination is completed, the release device may continuously intake air from the surroundings but will stop heating the air. The intake air may include excess hydrogen peroxide from the environment. The intake air will no longer be directed to the cylindrical cassette with powder hydrogen peroxide during this part of the process. Instead, the air will flow to a secondary cylindrical cassette. The secondary cylindrical cassette may include a catalyzer that decomposes vaporized hydrogen peroxide into water and oxygen.

In some non-limiting embodiments, the water and oxygen from decomposed hydrogen peroxide are captured within the release device and/or released into the surroundings. The residual vaporized hydrogen peroxide in the cylindrical cassette placed at site (1) may be released or captured after bio-decontamination is complete. The air intake may switch to the secondary cylindrical cassette at site (6) after completion of the de-contamination process, which causes air flow of the main cylindrical cassette at site (1) to stop. The release device may be configured with one or more sensors to detect hydrogen peroxide levels in the surroundings to signal completion of bio-decontamination by, for example, activating a display device (a screen (8), one or more LED indicators, and/or the like) and/or generating an audible notification.

Figure 17:
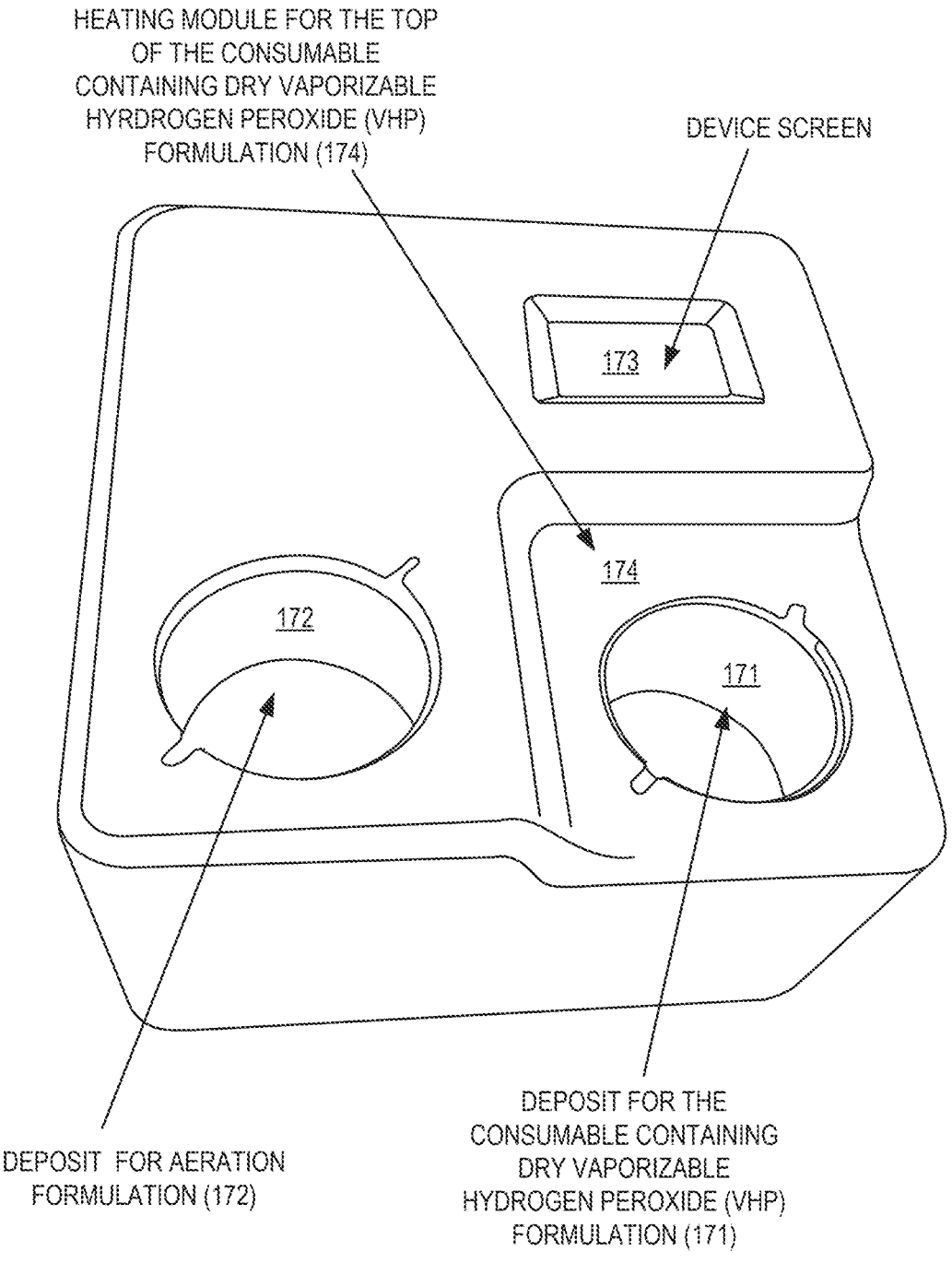

FIG. 17 shows a non-limiting embodiment of a release device. The release device includes a deposit cavity 171 for depositing a material containing dryVHP, a deposit cavity 172 for an aeration formulation, a display screen 173 for displaying one or more parameters, and a heating module 174 for heating the dryVHP material.

Although non-limiting embodiments have been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A release device, comprising
   a housing including an inlet and an outlet, the inlet configured to intake air from an environment external to the release device;
   a heating element arranged in the housing;
   a cartridge comprising a powdered hydrogen peroxide formulation arranged on top of a filter;
   a cavity positioned above the heating element and configured to receive the cartridge containing the powdered hydrogen peroxide formulation;
   a first fan arranged to move air into the inlet and around the heating element such that the air is heated and fluidizes the powdered hydrogen peroxide formulation; and
   a second fan arranged to move vapor out of the outlet into the environment external to the release device.

2. The release device of claim 1, wherein the heating element comprises a metallic plate.

3. The release device of claim 1, wherein the first fan is arranged below the heating element.

4. The release device of claim 1, wherein the housing comprises a lid, and wherein the second fan is arranged in the lid.

5. A release device comprising:
   a cartridge comprising a powdered hydrogen peroxide formulation arranged on top of a filter;
   a cavity adapted to receive the cartridge comprising the powdered hydrogen peroxide formulation;

an air intake configured to intake air from an environment external to the release device;

a first tan configured to deliver the intake air to the cartridge when the cartridge is arranged inside the cavity;

a heating element configured to heat air received through the air intake from the environment and to pass the heated air through the powdered hydrogen peroxide formulation in the cartridge placed in the cavity to fluidize the powdered hydrogen peroxide formulation and release hydrogen peroxide-enriched air; and a second fan configured to release the hydrogen peroxide-enriched air into the environment external to the release device.

6. The release device of claim 5, further comprising:

a second cavity adapted to receive a second cartridge comprising a catalyzer material; and a controller configured to alter an airflow from the air intake to the second cavity to bypass the first cavity.

7. The release device of claim 5, further comprising a controller in communication with and configured to control operation of the heating element, the first fan, and the second fan.

* * * * *